(12) United States Patent
Dalmasso

(10) Patent No.: US 8,765,398 B2
(45) Date of Patent: Jul. 1, 2014

(54) BIOLOGICAL INDICATOR WITH INTEGRAL PACKAGE

(75) Inventor: Joseph P. Dalmasso, Apex, NC (US)

(73) Assignee: Mesa Laboratories, Inc., Lakewood, CO (US)

( * ) Notice: Subject to any disclaimer, the term of this patent is extended or adjusted under 35 U.S.C. 154(b) by 364 days.

(21) Appl. No.: 13/067,123

(22) Filed: May 11, 2011

(65) Prior Publication Data

US 2011/0281296 A1    Nov. 17, 2011

Related U.S. Application Data

(60) Provisional application No. 61/395,359, filed on May 12, 2010.

(51) Int. Cl.
| | |
|---|---|
| *C12Q 1/22* | (2006.01) |
| *C12M 1/34* | (2006.01) |
| *C12M 1/02* | (2006.01) |
| *C12N 13/00* | (2006.01) |

(52) U.S. Cl.
USPC ... 435/31; 435/4; 435/29; 435/41; 435/287.1; 435/287.4

(58) Field of Classification Search
None
See application file for complete search history.

(56) References Cited

U.S. PATENT DOCUMENTS

| | | |
|---|---|---|
| 5,620,656 A | 4/1997 | Wensky et al. |
| 5,759,848 A | 6/1998 | Nagoshi et al. |
| 5,856,118 A | 1/1999 | Dalmasso |
| 6,037,168 A | 3/2000 | Brown |
| 8,211,663 B2 * | 7/2012 | Dallmier et al. ............ 435/31 |
| 2008/0206801 A1 * | 8/2008 | Dallmier et al. ............ 435/29 |
| 2009/0166237 A1 | 7/2009 | Gaskell et al. |
| 2009/0305334 A1 * | 12/2009 | Dallmier et al. ............ 435/29 |

FOREIGN PATENT DOCUMENTS

| | | | |
|---|---|---|---|
| EP | 2569413 A1 * | 3/2013 | |
| WO | 95/06134 A1 | 3/1995 | |
| WO | 97/05274 A1 | 2/1997 | |
| WO | 2007/046865 A1 | 4/2007 | |
| WO | WO 2011142824 A1 * | 11/2011 | |

OTHER PUBLICATIONS

Autoclave Testing Services, Inc, ATS brochure, 2010, 2 pages.*
McCauley, Kurt "End User—Proper BI Placement During VHP Decontamination Cycles" SporeNews: Biological Indicators Newsletter, Sep. 2009, 9(5), 4 pages.*

* cited by examiner

*Primary Examiner* — Chris R Tate
*Assistant Examiner* — Aaron J Kosar
(74) *Attorney, Agent, or Firm* — Breiner & Breiner, L.L.C.

(57) ABSTRACT

A biological indicator for determining the effectiveness of a sterilization process is disclosed having a package and carrier integral therewith. The package includes a first sheet and a second sheet having a bottom portion, side portions and a top portion. The first and second sheets are joined together generally along a periphery of the first and second sheets by a peelable adhesive. A carrier having a plurality of spores thereon for determining the effectiveness of a sterilization process is attached to the package between the first and second sheets and at least a portion of the resealable adhesive. The package may be opened and subsequently partially or fully closed to enclose the carrier.

18 Claims, 2 Drawing Sheets

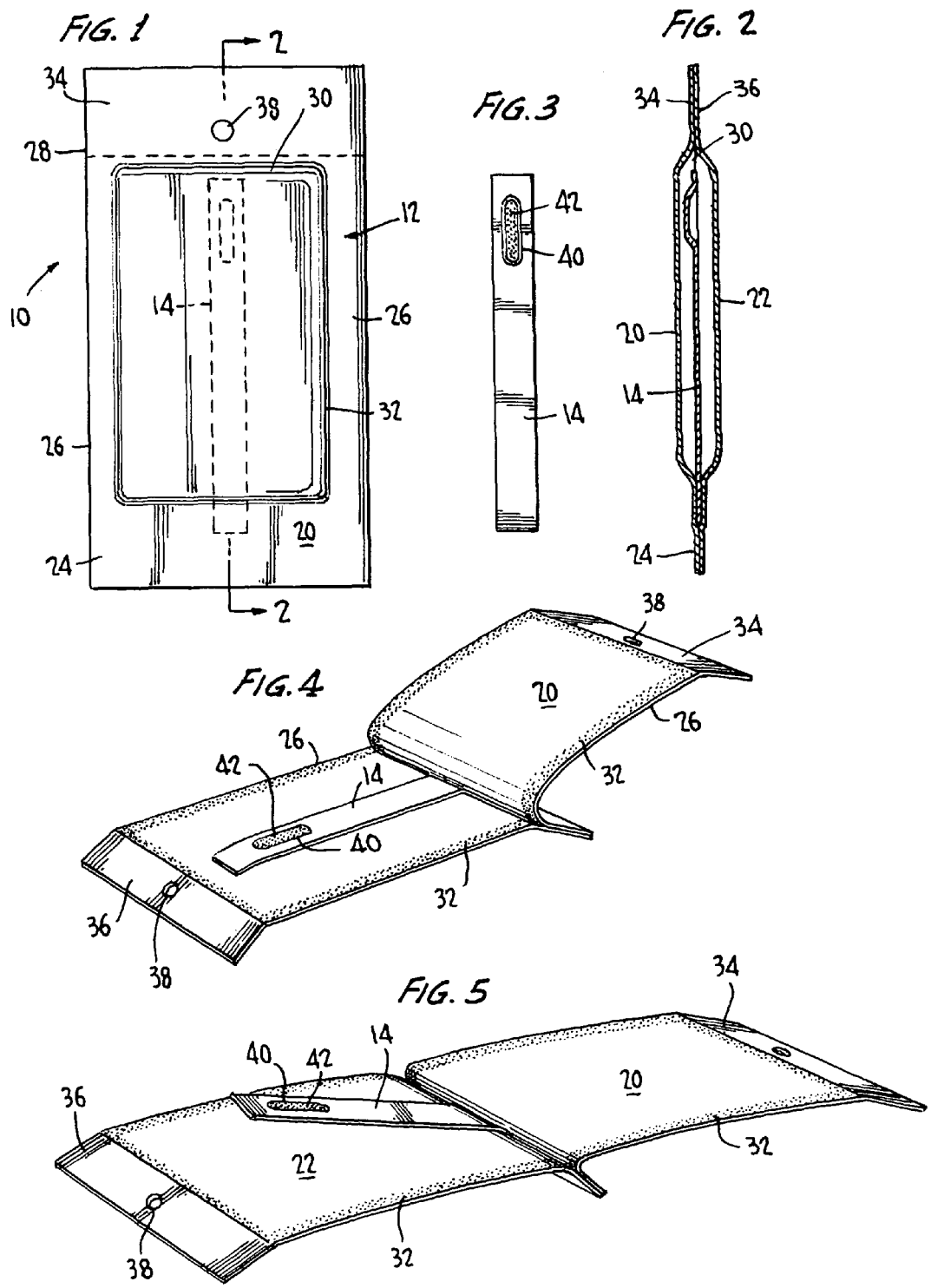

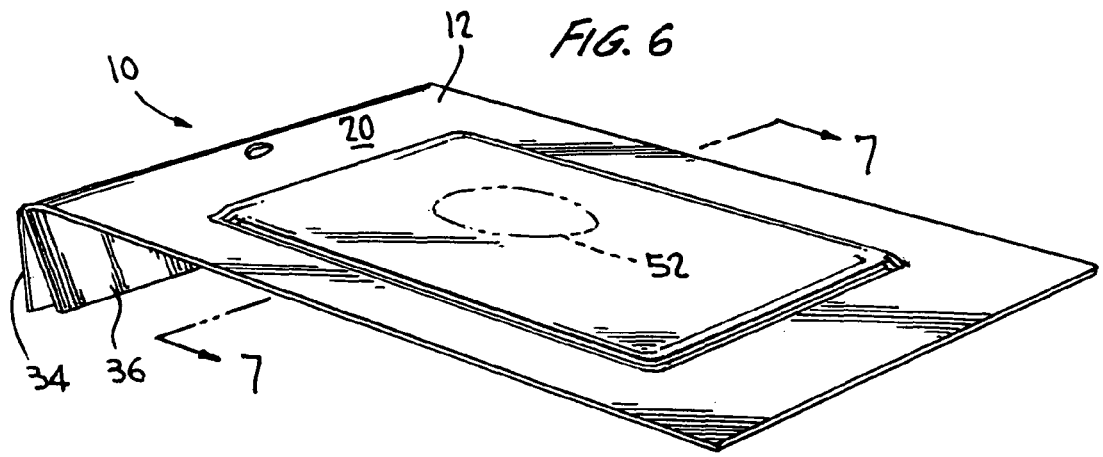
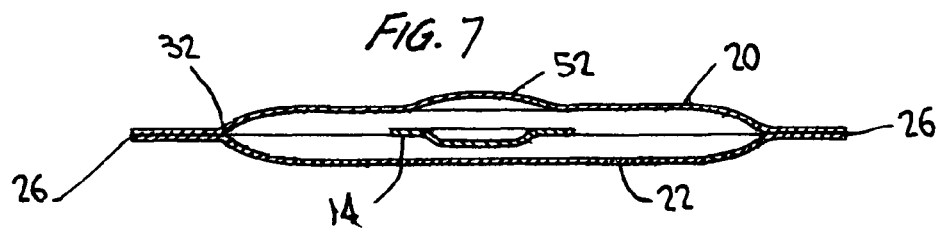
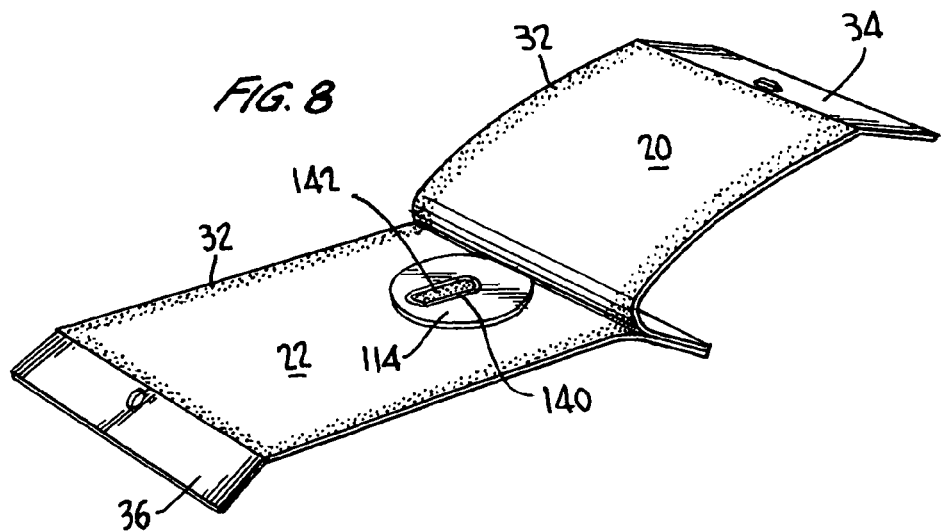

US 8,765,398 B2

BIOLOGICAL INDICATOR WITH INTEGRAL PACKAGE

RELATED APPLICATION

This application hereby claims the benefit under 35 U.S.C. §119(e) of Provisional Application Ser. No. 61/395,359, filed May 12, 2010, entitled "BIOLOGICAL INDICATOR INTEGRAL TO PERMEABLE PACKAGING," which application is incorporated herein by reference in its entirety.

FIELD OF THE INVENTION

The present invention relates to biological indicators (BI) for determining the effectiveness of a sterilization cycle and methods of use thereof. More particularly, the invention is directed to BIs including a carrier inoculated with bacterial spores and an integral package therefor.

BACKGROUND OF THE INVENTION

The use of BIs for verifying the effectiveness of a sterilization or decontamination cycle or process in health care, pharmaceutical, food processing and related fields is well known. Typically, these BIs include a known calibrated population of bacterial spores that are highly resistant to the sterilization process and are inoculated onto a carrier. The composition and use of such BIs have previously been described in my U.S. Pat. No. 5,856,118. This patent discloses a BI including a plurality of carriers inoculated with bacterial spores individually compartmentalized in a package. This patent is incorporated herein by reference in its entirety.

The BIs described in U.S. Pat. No. 5,856,118 include a sealed package that is permeable to gaseous vapors including hydrogen peroxide, yet provides a microbial barrier to an external environment. These "sealed" BIs are placed in a sterilization chamber and exposed to the sterilization process, the carrier inoculated with the bacterial spore remaining sealed within the package. The sealed package is opened after the sterilization process so that the carriers with the spores can be placed in a culture medium to test for survival of any of the inoculated spores on the carriers. Care must be taken when removing the inoculated carriers to ensure that microbial contaminants are not introduced to the culture medium. These contaminants could result in a "false positive" result if bacterial growth is observed in the culture medium implying that the sterilization process was ineffective.

Another type of BI includes an unpackaged inoculated carrier which is called "bare" BI. This type of BI also includes a carrier inoculated with spores, but is not contained within any individually sealed package during exposure to the sterilization cycle. These BIs may be placed within tubing or other restricted spaces prior to exposure to the sterilization cycle. Bare BIs having carriers in strip form are available from Apex, a Division of Mesa Laboratories of Bozeman, Mont. and are provided in a protective package. These strip BIs are not individually sealed. Rather, the strip BI is removed from a protective sleeve and placed in a chamber for the sterilization process. The strip BI is not influenced by a package during the sterilization process. However, with this type of BI, there is a possibility for microbial contamination due to handling in an environment outside of the sterilization chamber. This contamination may be both from spores escaping into the environment from the BI, or contamination of the BI with external microbes leading to false positive test results during culturing.

The above-referenced BIs have been found quite useful in determining the effectiveness of sterilization cycles. However, these BIs can be improved upon by providing BIs having an integral package as described in the present invention.

SUMMARY OF THE INVENTION

An object of the present invention is to provide BIs for determining the effectiveness of sterilization cycles and methods of use thereof.

Another object of the present invention is to provide BIs having an integral package which provides resistance to microbial contamination and prevents inadvertent contamination thereof.

Another object of the present invention is to provide BIs which are easy to handle and use in a sterilization process.

Another object of the present invention is to provide BIs having a carrier inoculated with bacterial spores and an integral package wherein the carrier remains attached to the package during the sterilization cycle.

Another object of the present invention is to provide BIs having a carrier inoculated with bacterial spores and an integral package wherein the carrier remains attached to the package during the sterilization cycle and which package may be partially or fully closed upon removal from the sterilization chamber.

The present invention is directed to a BI comprising a package and carrier integral therewith. The package includes a first sheet and a second sheet having a bottom portion, side portions and a top portion. The first and second sheets are joined together generally along a periphery of the first and second sheets by a peelable adhesive. The adhesive is preferably a resealable adhesive, but may include a permanent adhesive provided that it allows the first and second sheets to peel apart without destroying the package. A carrier having a plurality of spores thereon for determining the effectiveness of a sterilization process is attached to the package between the first and second sheets and at least a portion of the peelable adhesive. The package may be opened and subsequently partially or fully closed when using a resealable peelable adhesive along the periphery of the first and second sheets. In the alternative, the sides of the sheet material may be folded over to enclose the carrier when using a permanent peelable adhesive.

The present invention is further directed to a method of determining the effectiveness of a sterilization process. The method comprises the use of a BI having a package and a carrier integral therewith. The package includes a first sheet and a second sheet including a bottom portion, side portions and a top portion. The first and second sheets are joined together generally along a periphery of the first and second sheets by a peelable adhesive as described above. A carrier having a plurality of spores thereon for determining the effectiveness of the sterilization process is attached to the package between the first and second sheets and at least a portion of the peelable adhesive. The package may be opened and subsequently closed. The method includes opening the package from the top portion by pulling the first and second sheets to release the first or second sheet from each other by the peelable adhesive and exposing the carrier. The BI is then placed in a sterilization chamber for determining the effectiveness of a sterilization process. After completion of the sterilization process, the package is closed, i.e. covering the carrier, by rejoining at least a portion of the first and second sheets of the package when using a resealable peelable adhesive. In the alternative, the sides of the sheet material may be folded over to enclose the carrier when using a permanent peelable adhesive.

These primary objects and other objects of the invention will be apparent from the following description of the preferred embodiments of the invention and from the accompanying drawings.

BRIEF DESCRIPTION OF THE DRAWINGS

The following detailed description of specific non-limiting embodiments of the present invention can be best understood when read in conjunction with the following drawings, where like structures are indicated with like reference numbers.

FIG. 1 is a front view of a BI of the present invention and showing the carrier of the BI in phantom lines.

FIG. 2 is a cross-sectional side view taken along the line 2-2 of FIG. 1.

FIG. 3 is a front view of a carrier of the BI of FIG. 1.

FIG. 4 is a perspective view of the BI of FIG. 1 with the package opened, thereby partially exposing the carrier to the environment.

FIG. 5 is a perspective view of the BI of FIG. 1 showing the carrier ready for exposure in a sterilization cycle.

FIG. 6 is a perspective view of the BI of the present invention of FIG. 1 with the package closed after exposure to a sterilization cycle and showing an alternative embodiment in phantom lines as referenced in FIG. 7.

FIG. 7 is a cross-sectional view of another embodiment of the BI of the present invention taken along lines 7-7 of FIG. 6.

FIG. 8 is a perspective view of another embodiment of the BI of the present invention with the package opened to expose the carrier thereof.

BRIEF DESCRIPTION OF THE PREFERRED EMBODIMENTS

Referring to FIGS. 1-8, the present invention is directed to a BI 10 comprising a package 12 and a carrier 14. The package 12 provides a microbial barrier for the carrier 14 of the BI 10. In a preferred embodiment, the package 12 is made of a non-woven spunbond fiber material, such as Tyvek® material manufactured by E.I. du Pont de Nemours and Company. The material of the package 12 is lightweight, strong, difficult to tear, permeable to gas and water vapor and non-permeable to liquid.

The package 12 includes two sheets 20 and 22 of material or a single folded sheet of material forming two separate and aligned portions of the package 12. The package 12 will be described hereafter in terms of having two separate sheets of material forming a rectangular shaped package but such description applies to other embodiments, including a package formed from a single folded sheet of material, a plurality of sheets of material or other shapes. The package 12 includes a bottom 24, sides 26 and top 28 that includes an opening 30 for receiving carrier 14 as described hereafter.

The first sheet 20 and the second sheet 22 of the package 12 are sealed together along the bottom 24 and sides 26 by any suitable means for providing a sealed package including a thermal adhesive or mechanical processes such as tongue and groove or zipper mechanisms. In the preferred embodiment, an adhesive 32 is used which provides a peelable seal and allows opening and subsequent closing of the package 12 as described below. The adhesive is preferably a resealable adhesive allowing the first and second sheets to be resealed after the package has been opened. However, a permanent adhesive may be used provided that it allows the first and second sheets to be peeled apart without destroying the package. The resealable and permanent adhesives will be referred to herein as a "peelable adhesive." More particularly, the first sheet 20 and the second sheet 22 are sealed together with peelable adhesive 32 generally around a periphery of the package. Once the bottom and sides of the package 12 are sealed, the carrier 14 is inserted into the package 12 through opening 30 in top 28 as described in further detail hereafter. Thereafter, the top portion is sealed by the peelable adhesive 32 to close the package.

The top portion 28 may include flaps 34 and 36 for grasping to open the package 12 to expose the carrier 14 for use in the sterilization process. Additionally, the package 12 may also include a hole 38 in the flaps 34 and 36 for hanging or temporarily fixing the package 12 in a desired position either before or after opening the package.

The carrier 14 may include a well 40 in a portion thereof. The well 40 includes a plurality of spores 42 which are inoculated thereon as is known in the art of making BIs. The carrier 14 is made from a material such as steel, plastic, polymer, ceramic or other substrates known in the art. The carrier 14 is preferably a strip, but may also be a disk or any other suitable shape. The carrier 14 must have sufficient rigidity to be inserted into package 12 at bottom 24 permitting penetration of the peelable adhesive 32 to hold the carrier in place as described hereafter.

The carrier 14 is integral with package 12. It is inserted through the opening 30 and held in place between sheets 20 and 22 upon forced penetration of the peelable adhesive 32. Once the carrier 14 is positioned inside the package 12, the opening 30 of the package 12 is sealed by the peelable adhesive 32. The package preferably includes a puckered area between the first and second sheets such that there is space between sheet 20 and well 40 of carrier 14 to prevent abrasion and removal of inoculated spores from the substrate material being used.

The carrier 14 remains completely sealed inside the package 12 until the BI 10 is ready for use in the sterilization process. The BI 10 is then opened inside the sterilization chamber just prior to exposure to the sterilization process. More particularly, a user's thumb is positioned between the two flaps 34 and 36 of the package 12. The user grasps each of flaps 34 and 36 to prepare to break the seal formed by the peelable adhesive 32 at the top 28 of the package 12. The user exerts an outward force, e.g., pulls, on each of flaps 34 and 36, thereby breaking the seal of the package 12 adjacent to the flaps 34 and 36 and continues to pull sheet 20 away from sheet 22. This opens the package 14 to expose the carrier 14 containing the spores 42.

As shown in FIGS. 4 and 5, once the package 12 is opened, the portion of the carrier 14 opposite the well 40 remains loosely adjacent sheet 22 of the package 12 and opposite sheet 20. Accordingly, carrier 14 remains attached to package 12 during the sterilization process. As shown in FIG. 5, the opened BI 10 may be kept in a "V" shape configuration and then positioned on its side in the sterilization chamber to permit exposure to gas from the sterilization cycle without contaminating the carrier 14. The opened BI 10 may also be mechanically affixed in the sterilization chamber. For example, double-stick tape may be used to affix the outer surface of the package 12 to the inside of the sterilization chamber while keeping the inside of the package 12 completely exposed to the sterilization process.

Referring to FIG. 6, after exposure to the sterilization process, the package 12 may be partially or completely resealed when using a resealable peelable adhesive to enclose carrier 14 prior to removal from the sterilization chamber. In the alternative, the sides of the sheet material may be folded over to enclose the carrier when using a permanent peelable adhesive. This provides for better resistance to microbial contamination of the environment and prevents inadvertent contamination of the carrier 14 of the BI 10. Further, the flaps 34 and 36 may be folded to keep the package 12 enclosed around the carrier 14 and to minimize the transfer of contamination into or out of the BI during removal and transport to a post-sterilization culture location. This minimizes the chance for any microbes which were not killed in the BI from contaminating the area outside of the sterilization chamber after testing. It also prevents contamination of the BI prior to determining the results of the sterilization process. These contaminants may lead to false positive results erroneously indicating that the sterilization process was unsuccessful. The package is then taken to a culturing area to determine the effectiveness of the sterilization cycle. The carrier 14 is removed from the package for culturing. Removal is preferably by cutting or severing the bottom holding end of the carrier from the inoculated test portion of the carrier. However, sheets 20 and 22 may be completely separated and the carrier removed for culturing.

Referring to FIGS. 6 and 7, another embodiment of the BI 10 is shown. Specifically, FIG. 6 shows the BI 10 of FIG. 1 having a domed portion 52 in phantom lines. FIG. 7, taken along line 7-7 of FIG. 6, shows this alternative embodiment. The package 12 of FIG. 7 includes a dome area 52 in the region adjacent to the well 40 of the carrier 14 to further prevent the package 12 from contacting the spores 42 on the carrier 14. The dome 52 may be formed from a flexible permeable material, a rigid material such as a metal, a polymer, a ceramic material, or other similar materials.

Since the package 12 of the BI 10 is sealed prior to exposure to the sterilization cycle, the BI 10 may be easily handled during shipping or in the environment outside of the sterilization chamber without contaminating the carrier 14 or allowing the spores 42 to escape from the carrier 14.

In another embodiment of the invention (not shown), the carrier 14 may be completely removed from the package 12 by peeling either of sheets 20 or 22 of package 12 away from the carrier 14 by means of the peelable adhesive 32. Thereafter, the carrier 14 may be removed and placed in the sterilization chamber. After the sterilization process, the carrier may be placed back in package 12 and sheets 20 and 22 may be partially or fully resealed along the package peripherally when using a resealable peelable adhesive 32. In the alternative, sheets 20 and 22 may be folded over to enclose the carrier 14 when using a permanent peelable adhesive.

FIG. 8 illustrates a further alternative embodiment of the BI 10 of the invention. In this embodiment, the carrier 114 is a disk shape having a well 140 therein containing spores 142 as set forth above. A portion of the disk carrier 114 includes a spoon handle end (not shown) which is sealed between sheets 20 and 22 of the package 12 as described above for carrier 14. This spoon handle configuration permits the removal of the inoculated test portion of the indicator, preferably by cutting or severing, for subsequent culturing in growth media.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

It is claimed:

1. A biological indicator for determining the effectiveness of a sterilization process comprising:
    a package having a first sheet and a second sheet including a bottom portion, side portions and a top portion,
    said first and second sheets being joined together along a periphery of said first and second sheets by a peelable adhesive, and
    a carrier having a plurality of spores thereon for determining the effectiveness of said sterilization process and attached to said package between said first and second sheets and to at least a portion of said peelable adhesive,
    wherein said package may be opened and subsequently partially or fully closed to enclose said carrier.

2. The biological indicator of claim 1 wherein the peelable adhesive is a resealable adhesive wherein said package may be opened and subsequently partially or fully closed by said resealable adhesive along said periphery of said first and second sheets.

3. The biological indicator according to claim 1 wherein said carrier is attached to said package at the bottom portion of said package.

4. The biological indicator according to claim 3 wherein said top portion of said package includes first and second flaps.

5. The biological indicator according to claim 1 wherein said carrier is constructed and arranged of a sufficiently rigid material to penetrate said peelable adhesive between said first and second sheets.

6. A biological indicator according to claim 1 wherein said carrier includes a well for holding said plurality of spores.

7. The biological indicator according to claim 6 wherein said carrier comprises of strip and is made from a material selected from the group consisting of steel, plastic, polymer, ceramic or a combination thereof.

8. The biological indicator according to claim 1 wherein said first and second sheets are made of a non-woven spun-bond fiber material.

9. The biological indicator according to claim 1 wherein said package includes at least one additional sheet.

10. The biological indicator of claim 1 wherein said carrier comprises a disk.

11. A method of using a biological indicator for determining the effectiveness of a sterilization process comprising:
    (a) providing a biological indicator having a package having a first sheet and a second sheet including a bottom portion, side portions and a top portion, said first and second sheets being joined together along a periphery of said first and second sheets by a peelable adhesive, and a carrier having a plurality of spores thereon for determining the effectiveness of said sterilization process and attached to said package between said first and second sheets and to at least a portion of said peelable adhesive, wherein said package may be opened and subsequently closed to enclose said carrier,
    (b) opening said package from said top portion by pulling said first and second sheets to release said first or second sheet from each other by said peelable adhesive and exposing said carrier,
    (c) placing said biological indicator in a sterilization chamber and subjecting said biological indicator to said sterilization process for determining the effectiveness of said sterilization process, and
    (d) after completion of said sterilization process, partially or fully closing said package to enclose said carrier.

12. A method according to claim 11 wherein the peelable adhesive is a resealable adhesive and said package is opened and subsequently partially or fully closed by said resealable adhesive along said periphery of said first and second sheets.

13. A method according to claim 11 wherein said carrier is attached to said package at the bottom portion of said package.

14. A method according to claim 13 wherein said top portion of said package includes first and second flaps.

15. A method according to claim 11 wherein said carrier include's a well for holding said plurality of spores.

16. A method according to claim 15 wherein said carrier comprises of strip and is made from a material selected from the group consisting of steel, plastic, polymer, ceramic or a combination thereof.

17. A method according to claim 11 wherein said first and second sheets are made of a non-woven spunbond fiber material.

18. A method according to claim 11 wherein said carrier comprises a disk.

* * * * *